(12) United States Patent
Marban et al.

(10) Patent No.: US 6,521,617 B2
(45) Date of Patent: Feb. 18, 2003

(54) TREATMENT OF APOPTOTIC CELL DEATH

(75) Inventors: Eduardo Marban, Lutherville, MD (US); Brian O'Rourke, Sparks, MD (US); Masaharu Akao, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/977,558

(22) Filed: Oct. 15, 2001

(65) Prior Publication Data

US 2002/0091144 A1 Jul. 11, 2002

Related U.S. Application Data

(60) Provisional application No. 60/240,267, filed on Oct. 13, 2000.

(51) Int. Cl.[7] .......................... A61K 31/54; A61K 31/44
(52) U.S. Cl. ...................... 514/223.2; 514/344; 514/355
(58) Field of Search ............................... 514/223.2, 344, 514/355

(56) References Cited

U.S. PATENT DOCUMENTS 6,183,948 B1 * 2/2001 Marban et al. ................ 435/4
6,313,112 B1 * 11/2001 Busija ..................... 514/223.2

* cited by examiner

*Primary Examiner*—Raymond Henley, III
(74) *Attorney, Agent, or Firm*—Edwards & Angell, LLP; Peter F. Corless; Dianne M. Rees

(57) ABSTRACT

New methods are provided for treating against apoptotic cell death, including apoptotic cardiac and neuronal cells. Therapies of the invention include administration of a mitochondrial oxidizer compound to a subject in need thereof, such as a subject suffering from or susceptible to stroke, heart attack, brain or spinal cord trauma, or chronic conditions that can resulting apoptotic cell death such as a neurodegenerative disease.

39 Claims, 4 Drawing Sheets

TREATMENT OF APOPTOTIC CELL DEATH

The present application claims the benefit of U.S. provisional application No. 60/240,267 filed Oct. 13, 2000, which is incorporated herein by reference in its entirety.

STATEMENT OF U.S. GOVERNMENT SUPPORT

Funding for the present invention was provided in part by the Government of the United States by virtue of a National Institutes of Health grant. Accordingly, the Government of the United States has certain rights in this invention.

FIELD OF THE INVENTION

The invention provides new methods for treating against apoptotic cell death, including apoptotic cardiac and neuronal cells. Therapies of the invention include administration of a mitochondrial oxidizer compound to a subject in need thereof, such as a subject suffering from or susceptible to stroke, heart attack, brain or spinal cord trauma, or chronic conditions that can result in apoptotic cell death such as neurodegenerative disease.

BACKGROUND OF THE INVENTION

Acute ischemic syndromes, notably heart attack and stroke, remain the leading causes of death and disability in developed countries.

Nerve cell death (degeneration) can cause potentially devastating and irreversible effects for an individual and may occur e.g. as a result of stroke, heart attack or other brain or spinal cord ischemia or trauma. Additionally, neurodegenerative disorders involve nerve cell death (degeneration) such as Alzheimer's disease, Parkinson's disease, Huntington's disease, Amyotrophic Lateral Sclerosis, Down's Syndrome and Korsakoff's disease.

It would be desirable to have new therapies for treatment against such indications.

SUMMARY OF THE INVENTION

We now provide therapies for treatment against apoptotic cell death. In particular, we have discovered that mitochondrial $K_{ATP}$ channel activation can effectively inhibit apoptosis in a variety of cells, including cardiac and neuronal cells.

Methods of the invention include treatment of mammalian cells, particularly primate cells especially human cells with one or more compounds that can modulate mitochondrial function, particularly compounds that can positively impact mitochondrial function and increase cell energy output. Such compounds are referred to herein as "mitochondrial oxidizer compounds" or "mito$K_{ATP}$ channel opening compounds" or other similar term and can be identified e.g. by assays disclosed herein as well as in U.S. Pat. No. 6,183,948 to Marban et al. Specifically preferred mito$K_{ATP}$ channel opening compounds for use in the methods of the invention include diazoxide, pinacidil, nicorandil, and BMS 191095, or compounds which confer protection that can be inhibited by 5-hydroxydecanoate (a mito$K_{ATP}$ antagonist).

Methods of the invention particularly include treating cells that are apoptotic or otherwise undergoing programmed cell death, or at risk to undergo such programmed cell death. Ventricular cells and neuronal cells are particularly suitable for treatment in accordance with the invention. For example, a subject suffering from or susceptible to heart failure can be treated in accordance with the invention.

Additionally, a subject suffering from a condition involving programmed cell death of neuronal cells can be treated in accordance with the invention, particularly to treat a subject suffering from stroke, spinal cord injury or a neurodegenerative disease such as Alzheimer's disease, Parkinson's disease, Huntington's disease, Amyotrophic Lateral Sclerosis, Down's Syndrome, Korsakoff's disease, cerebral palsy and/or age-dependent dementia.

Still further, the invention includes treatment of diabetes, including treatment of pancreatic beta cells, apoptosis of which can be involved with a subject suffering from diabetes.

Treatment methods of the invention include administration to a mammal in need of such treatment a therapeutically effective amount of one or more compounds that can positively impact mitochondrial function (i.e. mito$K_{ATP}$ channel opening compounds) to an animal, including a mammal, particularly a human. Preferably, a subject is identified and selected that is susceptible to or suffering from a condition associated with apoptotic cell death.

Other aspects of the invention are disclosed infra.

DETAILED DESCRIPTION OF THE INVENTION

Figure 1:
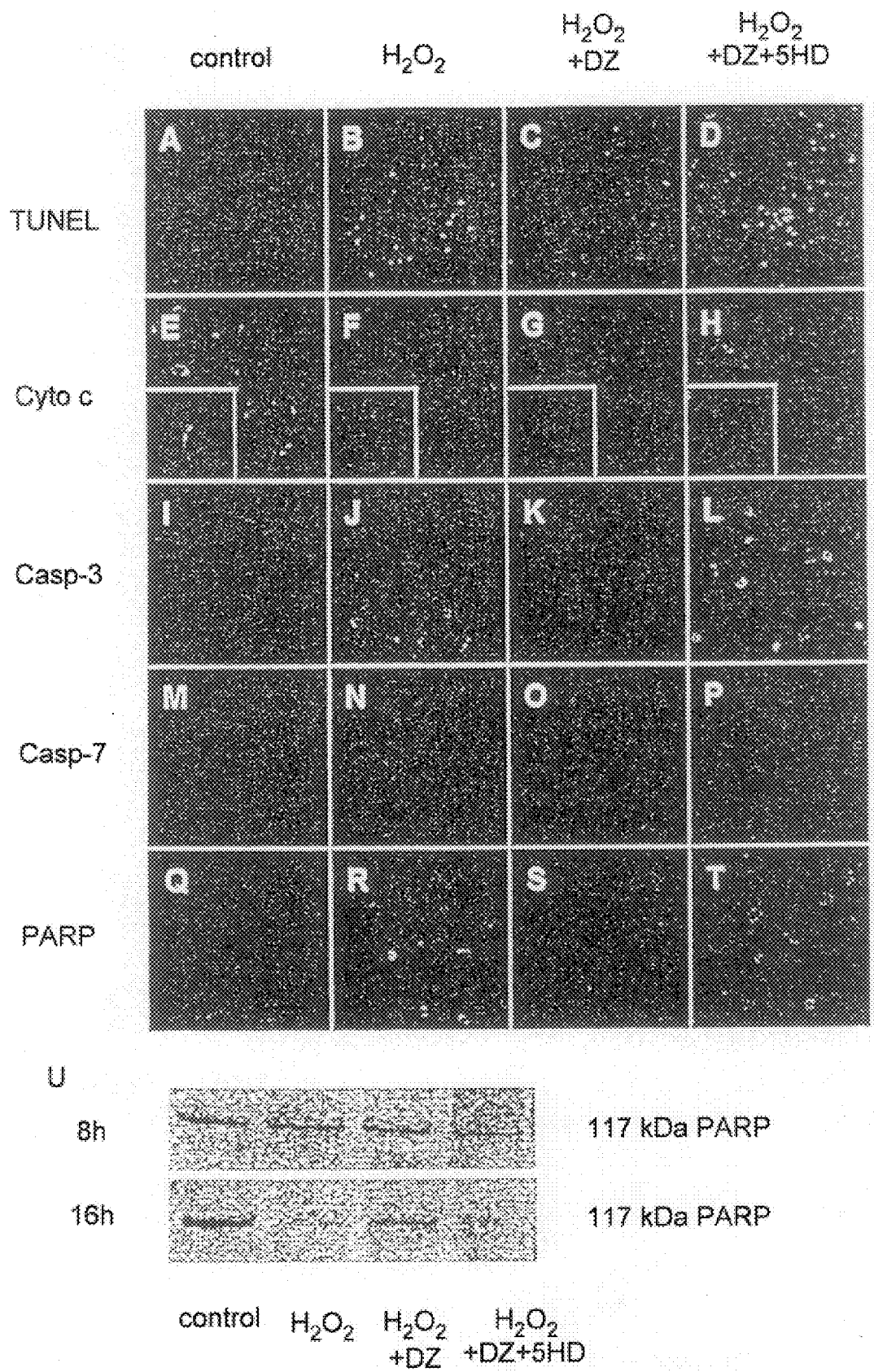
FIG. 1 (which includes FIGS. A through U). (A–D) TUNEL staining in neonatal rat cardiac myocytes. (A) Control cells show very sparse TUNEL positive nuclei. (B) Cells exposed to 200 $\mu$M $H_2O_2$ for 16 h become predominantly TUNEL-positive. (C) 100 $\mu$M diazoxide protects against $H_2O_2$-induced TUNEL positivity. (D) The protective effect of diazoxide is blocked by 500 $\mu$M of mito$K_{ATP}$ channel blocker 5-HD. (E–H) Cytochrome c translocation in neonatal rat cardiac myocytes. Each panel has a inset to show higher magnification. Blue fluorescent dye DAPI demonstrates the nuclear morphology. (E) Control cells show no translocation of cytochrome c to the cytosol. (F) Cells exposed to $H_2O_2$ exhibit extensive translocation of cytochrome c to the cytosol. (G) Diazoxide protects against $H_2O_2$-induced translocation of cytochrome c. (H) The protective effect of diazoxide is blocked by 5-HD. (I–L) Caspase-3 activation in neonatal rat cardiac myocytes. (I) Control cells show no caspase-3 activation. (J) Cells exposed to $H_2O_2$ become predominantly caspase-3 positive. (K) Diazoxide protects against $H_2O_2$-induced activation of caspase-3. (L) The protective effect of diazoxide is blocked by 5-HD (M–P) Caspase-7 activation in neonatal rat cardiac myocytes. (M) Control cells show no caspase-7 activation. (N) Cells exposed to $H_2O_2$ become predominantly caspase-7 positive. (O) Diazoxide protects against $H_2O_2$-induced activation of caspase-7. (P) The protective effect of diazoxide is blocked by 5-HD. (Q–T) PA-PP cleavage in neonatal rat cardiac myocytes. (Q) Control cells show no PARP cleavage. (R) Cells exposed to $H_2O_2$ become predominantly cleaved PARP positive. (S) Diazoxide protects against $H_2O_2$-induced cleavage of PARP. (T) The protective effect of diazoxide is blocked by 5-HD. (U) Immunoblot of PARP in neonatal rat cardiac myocytes. Cell lysates from each experimental group were subjected to immunoblot analysis (30 $\mu$g protein/lane) with monoclonal antibody against 117-kDa PARP holoenzyme. Cells were treated for either 8 h or 16 hours.

As stated above, and demonstrated in the examples which follow, it has now been found that mitoK$_{ATP}$ channel activation (opening) can be effective to treat against or inhibit apoptosis, including apoptosis induced by oxidative stress.

We have particularly found that activation of mitoK$_{ATP}$ channels can suppress programmed cell death. We also have found that opening of mitoK$_{ATP}$ channels can act early in the apoptotic cascade by inhibiting cytochrome c release and $\Delta\Psi$ depolarization (early alterations in the apoptotic cascade).

Therapeutic methods of the invention include selecting or identifying mammalian cells or a mammalian subject that that is suffering from or susceptible to apoptotic cell death, particularly as a result of oxidative stress and administering to the cells or subject effective amounts of one or more mitochondrial oxidizer compounds, such as diazoxide. Exemplary cells for treatment include various eukaryotic cells e.g. cardiac myocytes, neuronal cells and other non-differentiating cells.

Typical subjects for treatment include mammals suffering from or susceptible to ischemic insult, particularly heart attack, or other event involving cellular apoptosis, such as resulting from a neurodegenerative disease.

Preferred compounds for use in therapeutic methods of the invention can be readily identified. In particular, suitable identifying assays are disclosed in U.S. Pat. No. 6,183,948 to Marban et al. which includes assays for detecting compounds capable of modulating mitochondrial redox potential. The following assay of steps a) through d) is defined and referred to herein as a "standard mitochondrial redox assay":

a) provide a population or eukaryotic cells;
b) contact a first portion of the cells with one or more compounds that are candidate as activators of mitoK$_{ATP}$ channels;
c) contact a second portion of the cells with a known mitochondrial oxidizing compound (such as diazoxide); and
d) measure a difference between mitochondrial fluorescence produced in steps b) and c). Fluorescence can be detected as disclosed in U.S. Pat. No. 6,183,948 to Marban et al. such as by oxidation of nicotinamide adenine dinucleotide (NAD) or flavin adenine dinucleotide (FAD) moieties by means of e.g. fluorescence microscopy, photometry and photographic film.

Preferably, the above assay will identify a candidate mitochondrial oxidizer compound (mitoK$_{ATP}$ channel opening compound) that increases mitochondrial oxidation (e.g. as assessed by NAD or FAD fluorescence) by a detectable amount relative (e.g. as determined by fluorescent microscopy) relative to a control in a mitochondrial redox assay as set forth in steps a) through d) immediately above and in U.S. Pat. No. 6,183,948 relative to a control (i.e. the same assay where the candidate compound has not been exposed to test cells). In particular, preferably a mitoK$_{ATP}$ channel opening compound will be identified that increases mitochondrial oxidation (e.g. as assessed by NAD or FAD fluorescence and determined fluorescent microscopy) by at least about 10%, 20%, 30%, 40%, 50%, 60%, 70%, 80%, 90% or 100% in a mitochondrial redox assay as set forth in steps a) through d) immediately above and in U.S. Pat. No. 6,183,948 relative to a control (i.e. the same assay where the candidate compound has not been exposed to test cells).

The term "candidate compound" or candidate mitochondrial activator compound" or other similar term as used herein refers to any chemical compound that can be added to a eukaryotic cell, and may comprise a compound that exists naturally within the cell or is exogenous to the cell. The compounds include native compounds or synthetic compounds, and derivatives thereof. As discussed above, particularly preferred mitoK$_{ATP}$ channel opening compounds include diazoxide, pinacidil, nicorandil, and BMS 191095 (Bristol-Myers Squibb compound), or compounds which confer protection that can by inhibited by 5-hydroxydecanoate (a mitoK$_{ATP}$ antagonist). MitoKATP antagonists can be identified by methods disclosed in U.S. Pat. No. 6,183,948 (e.g. reduces oxidation potential).

As discussed above, the invention includes methods for treating or preventing certain neurological disorders, including the consequences of stroke, heart attack and traumatic head or brain injury, epilepsy or neurodegenerative diseases comprising the administration of an effective amount of one or more compounds of the invention to a subject including a mammal, such as a primate, especially a human, in need of such treatment. In particular, the invention provides methods for treatment and/or prophylaxis of nerve cell death (degeneration) resulting e.g. from hypoxia, hypoglycemia, brain or spinal cord ischemia, brain or spinal cord trauma, stroke, heart attack or drowning. Typical candidates for treatment include e.g. heart attack, stroke and/or persons suffering from cardiac arrest neurological deficits, brain or spinal cord injury patients, patients undergoing major surgery such as heart surgery where brain ischemia is a potential complication and patients such as divers suffering from decompression sickness due to gas emboli in the blood stream. Candidates for treatment also will include those patients undergoing a surgical procedure involving extracorporeal circulation such as e.g. a bypass procedure. Subjects suffering from or susceptible to peripheral neuropathy can be treated in accordance with the invention by administration of an effective amount of one or more compounds of one or more mitochondrial activator compounds as disclosed herein.

The invention in particular provides methods for treatment which comprise administration of one or more compounds of the invention to a patient that is undergoing surgery or other procedure where brain or spinal cord ischemia is a potential risk. For example, carotid endarterectomy is a surgical procedure employed to correct atherosclerosis of the carotid arteries. Major risks associated with the procedure include intraoperative embolization and the danger of hypertension in the brain following increased cerebral blood flow, which may result in aneurysm or hemorrhage. Thus, an effective amount of one or more compounds of the present invention could be administered pre-operatively or peri-operatively to reduce such risks associated with carotid endarterectomy, or other post-surgical neurological deficits.

The invention further includes methods for prophylaxis against neurological deficits resulting from e.g. coronary artery bypass graft surgery and aortic valve replacement surgery, or other procedure involving extra-corporeal circulation. Those methods will comprise administering to a patient undergoing such surgical procedures an effective amount of one or more compounds of the invention, typically either pre-operatively or peri-operatively.

Methods of the invention can be particularly useful in the treatment of mammalian subjects, e.g., humans, to provide neuroprotective therapy and/or prophylaxis. Typically, such subjects include those afflicted with neurodegenerative diseases such as Parkinson's disease, Huntington's disease, Amyotrophic Lateral Sclerosis, Alzheimer's disease, Down's Syndrome and Korsakoff's disease.

As discussed above, the invention also includes treatment of diabetes, including treatment of pancreatic beta cells, apoptosis of which can be involved with a subject suffering from diabetes. For example, one or more mitoK$_{ATP}$ channel opening compounds can be administered on a regular schedule (e.g. daily) to a mammal, particularly human suffering from diabetes.

The invention also provides methods for determining binding activity of compounds of the invention as well as in vitro and in vivo binding activity diagnostic methods e.g. using one or more radiolabelled compounds of the invention, e.g., a compound of the invention that is labeled with $^{125}$I, tritium, $^{32}$P, $^{99}$Tc, or the like, preferably $^{125}$I. For instance, a compound of the invention having a phenyl or other aryl substituent that is ring substituted with one or more $^{125}$I groups can be administered to a mammal and the subject then scanned for binding of the compound. Specifically, single photon emission computed tomography ("SPECT") can be employed to detect such binding. Such an analysis of the mammal could e.g. aid in the diagnosis and treatment of disorders involving cellular apoptosis. That is, a labeled compound of the invention will selectively bind to apoptotic cells e.g. a subject's brain or heart to differentiate between degenerating and non-degenerating tissue and thereby assess trauma or diagnosis a neurodegenerative condition and the extent thereof.

Accordingly, the invention includes compounds of the invention that contain a radiolabel such as $^{125}$I, tritium, $^{32}$P, $^{99}$Tc, or the like, preferably $^{125}$I. Such radiolabelled compounds can be suitably prepared by procedures known in the synthesis art. For example, a compound of the invention having an aromatic group, such as phenyl, that has a bromo or chloro ring substituent can be employed in an exchange labeling reaction to provide the corresponding compound having an $^{125}$I ring substituent.

Compounds for use in the methods of the invention can be administered intranasally, orally or by injection, e.g., intramuscular, intraperitoneal, subcutaneous or intravenous injection, or by transdermal, intraocular or enteral means. The optimal dose can be determined by conventional means. Compounds for use in the methods of the invention are suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc.

Compounds for use in the methods of the invention can be employed, either alone or in combination with one or more other therapeutic agents as discussed above, as a pharmaceutical composition in mixture with conventional excipient, i.e., pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For topical applications, formulations may be prepared in a topical ointment or cream containing one or more compounds of the invention. When formulated as an ointment, one or more compounds of the invention suitably may be employed with either a paraffinic or a water-miscible base. The one or more compounds also may be formulated with an oil-in-water cream base. Other suitable topical formulations include e.g. lozenges and dermal patches.

Intravenous or parenteral administration, e.g., subcutaneous, intraperitoneal or intramuscular administration are generally preferred.

For in vitro applications, a multi-well plate or other reaction substrate may be suitably employed.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. In general, a suitable effective dose of one or more compounds of the invention, particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule.

The following non-limiting examples are illustrative of the invention. All documents mentioned herein are incorporated herein by reference.

EXAMPLE 1

Neonatal rat cardiac myocytes in primary culture were randomly assigned to one of four experimental groups: 1) control group, 2) incubation with 200 $\mu$M $H_2O_2$, 3) 100 $\mu$M diazoxide, applied together with 200 $\mu$M $H_2O_2$, 4) 100 $\mu$IM diazoxide and 500 $\mu$M 5-HD, applied together with 200 $\mu$M $H_2O_2$. As an indicator of DNA fragmentation, FIG. 1A–D demonstrates TUNEL (terminal deoxynucleotidyl transferase (TdT)-mediated dUTP nick end-labeling) staining in each experimental group. Staining was conducted as follows. TUNEL staining was performed according to the manufacturer's protocol (Roche Molecular Biochemicals). Fluorescein labels incorporated in nucleotide polymers were detected by laser scanning confocal microscopy at excitation wavelength of 488 rim (argon laser). Cells were identified as apoptotic if they showed positive TUNEL staining in the nucleus. Necrotic cells had been excluded from these specimens since they became non-adherent and were removed when the medium was decanted and the cell layers were washed in PBS.

Control cells showed few TUNEL-positive nuclei (FIG. 1A), but exposure to 200 $\mu$M $H_2O_2$ for 16 h increased the number of TUNEL-positive nuclei (FIG. 1B). Diazoxide decreased the frequency of $H_2O_2$-induced TUNEL positive nuclei (FIG. 1C), indicating a protective effect of the mitoK$_{ATP}$ channel agonist. This effect was blocked by the mitoK$_{ATP}$ channel antagonist 5-HD (FIG. 1D). FIGS. 1E–H demonstrates cytochrome c immunofluorescence. That immunofluorescence was conducted as follows: cells were plated on glass coverslips, treated with drugs as indicated, fixed in ice-cold 1:1 mixture of methanol/acetone, blocked with 10% normal goat serum and 0.075% saponin in PBS, and incubated with primary antibody dissolved in blocking solution at a dilution of 1:100. For cytochrome c staining, mouse monoclonal anti-cytochrome c antibody (Pharmingen; 6H2.Ba4) was used; for caspase-3 staining, rabbit polyclonal antiserum raised against the activated form of caspase-3 (Pharmingen), which recognizes only the processed 20 kDa subunit of cleaved caspase-3, was used; for caspase-7 staining, rabbit polyclonal antiserum raised against the activated form of caspase-7 (New England Biolabs), which recognizes only the processed 20 kDa subunit of activated caspase-7, was used; and for PARP staining, rabbit polyclonal antiserum raised against the activated form of PARP (New England Biolabs), which recognizes only the processed 89 kDa subunit of cleaved PARP, was used. After washing coverslips with PBS, cells were incubated with secondary antibody consisting of Alexa Fluor 546 goat anti-mouse IgG, F(ab')$_2$ (Molecular Probes, diluted 1:100) or Alexa Fluor 546 goat anti-rabbit IgG, F(ab')$_2$ (Molecular Probes, diluted 1:100) respectively. Finally, cells were counterstained with the DNA binding dye DAPI (5 $\mu$M, Molecular Probes). These coverslips were mounted with antifading fluorescence mounting medium and were examined by a laser scanning confocal microscope (Zeiss, LSM 410), using 40x water-immersion lens and 2x optical zoom. Alexa 546 was excited and visualized by a helium/neon laser (543 nm), and DAPI by an UV laser (351 nm).

In control, the distribution of cytochrome c is reticular and punctate (FIG. 1E), indicative of a normal mitochondrial pattern. Incubation with 200 $\mu$M $H_2O_2$ for 16 hours induced cytochrome c translocation to the cytoplasm, resulting in a homogeneous distribution (FIG. 1F). Diazoxide inhibited the translocation of cytochrome c (FIG. 1G), while the addition of 500 $\mu$M 5-HD abrogated the effect of diazoxide (FIG. 1H). Counterstaining of nuclei with the blue fluorescent dye, DAPI, confirms the predominance of condensed and shrunken nuclei in the cells exhibiting cytochrome c translocation. FIGS. 1I–L demonstrates the inununofluorescent staining for caspase-3, visible as red, using polyclonal antiserum that recognizes only the active form of the enzyme. In control, cells showed little cytosolic fluorescence (FIG. 1I), but 200 $\mu$M $H_2O_2$ markedly increased the red signals (FIG. 1J). Incubation with 100 $\mu$M diazoxide inhibited the $H_2O_2$-induced activation of caspase-3 (FIG. 1K), while addition of 500-$\mu$iM 5-HD negated the effect of diazoxide (FIG. 1L). FIGS. 1M–P demonstrates staining for activated caspase-7. In parallel with caspase-3, diazoxide inhibited $H_2O_2$-induced activation of caspase-7 (FIG. 1O), and 5-HD again abolished the anti-apoptosic effect of diazoxide (FIG. 1P). Next, we examined poly(ADP-ribose) polymerase (PARP), one of the main targets of caspase-3 or 7 in vivo, using a polyclonal antibody which detects only the cleaved fragment of PARP (FIGS. 1Q–T). In parallel with the activation of caspases-3 or 7, PARP cleavage was augmented in $H_2O_2$ treated cells (FIG. 1R). Diazoxide inhibited the $H_2O_2$-induced PARP cleavage (FIG. 1S) and addition of 500 $\mu$M 5-HD prevented the diazoxide effect (FIG. 1T). These data show that oxidative stress induces apoptosis which is inhibited by mitoK$_{ATP}$ channel activation.

To confirm these findings using complementary methods, we examined PARP protein levels as a biochemical indicator of the activation of downstream caspases in each group. As shown in FIG. IU, the PARP holoenzyme was detested as a 117-kDa band on immunoblot. $H_2O_2$ exposure enhanced the cleavage of PARP, resulting in a loss of the holoenzyme band in a time-dependent manner. Diazoxide attenuates the loss of PARP holoenzyme, and 5-HD abolished the protective effect of diazoxide.

Figure 2A:
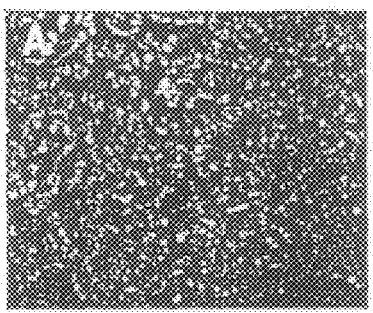
FIG. 2. Mitochondrial membrane potential ($\Delta\psi$) in neonatal rat cardiac myocytes. (A) Control cells show predominantly punctate red staining with a fluorescent dye, JC-1, indicative of normal mitochondrial uptake driven by a maintained $\Delta\psi$. (B) Cells exposed to 200 $\mu$M $H_2O_2$ for 2 h lose punctate red staining. (C) 100 $\mu$M diazoxide protects against $H_2O_2$-induced loss of $\Delta\psi$, as shown by the preservation of red signals. (D) The protective effect of diazoxide is blocked by 500 $\mu$M of mitoK$_{ATP}$ channel blocker 5-HD. (E) Quantitative analysis from low power confocal images. Lane 1: $H_2O_2$, lane 2: $H_2O_2$+diazoxide 20 $\mu$M, lane 3: $H_2O_2$+diazoxide 50 $\mu$M, lane 4: $H_2O_2$+diazoxide 100 $\mu$M, lane 5' $H_2O_2$+diazoxide 200 $\mu$M, lane 6: $H_2O_2$+diazoxide 100 $\mu$M+5-HD 500 $\mu$M. The concentration of $H_2O_2$ was 200 $\mu$M for all groups. Results are expressed as arbitrary units of red fluorescence intensity. The value of control group was 95.06. (F–I) Results of flow cytometry analysis. The histograms of FL-2 channel (red fluorescence) are shown. In all of the histograms, those from control group and 200 $\mu$M $H_2O_2$-treated group are overlayed as references. (F) $H_2O_2$+diazoxide 20 $\mu$M, (G) $H_2O_2$+diazoxide 50 $\mu$M, (H) $H_2O_2$+diazoxide 100 $\mu$M, (I) $H_2O_2$+diazoxide 100 $\mu$M+5-HD 500 $\mu$M, (J) $H_2O_2$+5-HD 500 $\mu$M. The results of flow cytometry analysis shown are representative data of three independent experiments.
Figure 2B:
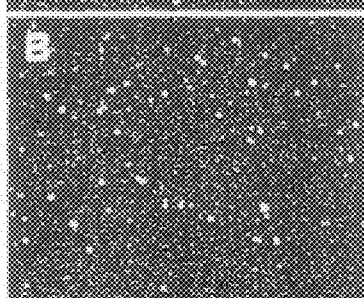
Figure 2C:
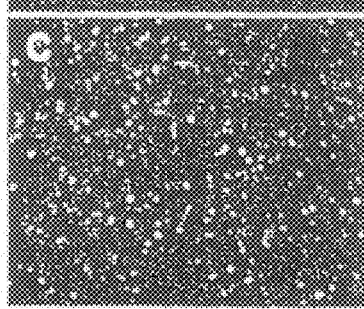
Figure 2D:
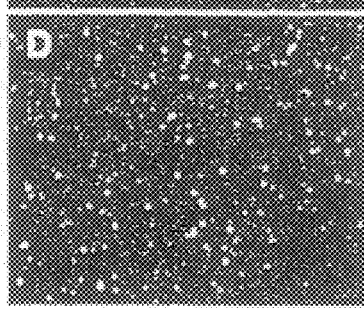
Figure 2E:
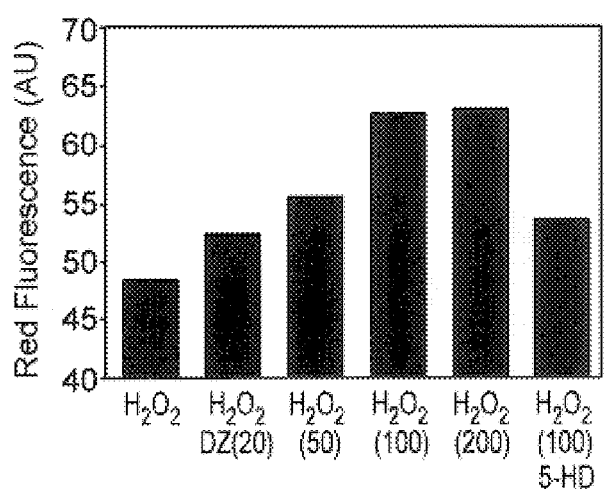

Redistribution of cytochrome c has been linked to the loss of mitochondrial membrane potential ($\Delta\psi$) and the opening of the mitochondrial permeability transition pore (23). We assessed $\Delta\psi$ in $H_2O_2$-stimulated myocytes using a fluorescent probe, JC-1 (24). Control cells exhibit punctate red staining (FIG. 2A), indicative of normal mitochondrial uptake driven by maintained $\Delta\psi$. Cells exposed to 200 $\mu$M $H_2O_2$ for 2 h lose punctate red staining (FIG. 2B), in favor of a diffuse green cytosolic signal indicative of the loss of $\Delta\psi$. Incubation with 100 $\mu$M diazoxide protects against $H_2O_2$-induced loss of mitochondrial integrity (FIG. 2C). The protective effect of diazoxide is blocked by 500 $\mu$M 5-HD (FIG. 2D). These observations were rendered quantitative by automated image analysis (24). FIG. 2E summarizes the red fluorescence, an indicator of $\Delta\psi$. Exposure to 200 $\mu$M $H_2O_2$ for 2 h resulted in mitochondrial depolarization, while diazoxide prevented loss of $\Delta\psi$ in a dose-dependent manner;

the $EC_{50}$ of=40 μM is close to the value of 27 μM for mitoK$_{ATP}$ channel activation in intact heart cells. Addition of 500 μM 5-HD antagonized the salutary effect of diazoxide.

Figure 2F:
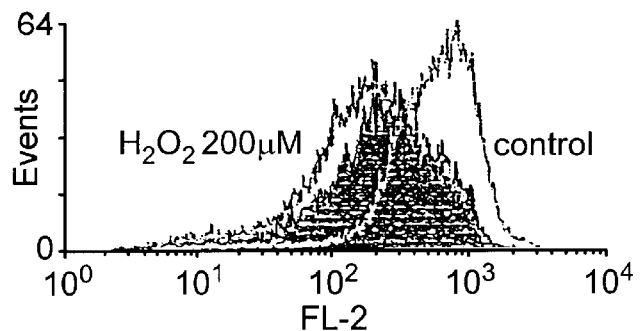
Figure 2G:
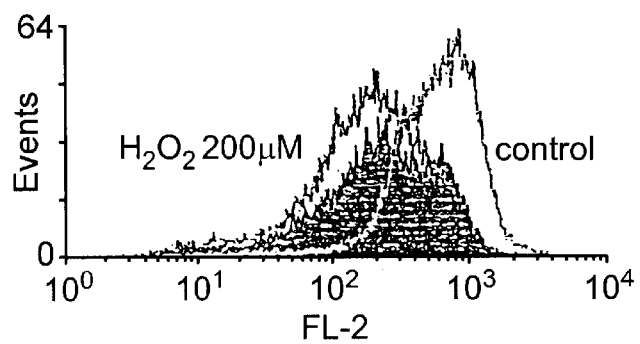
Figure 2H:
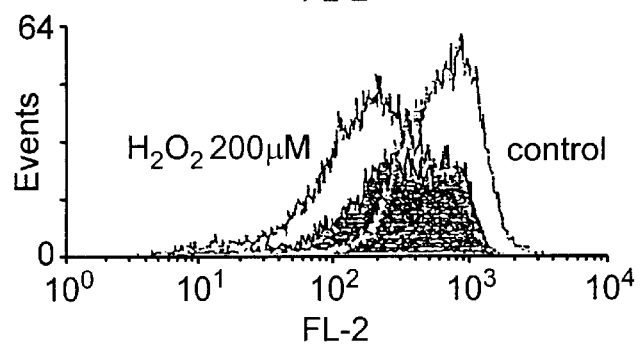
Figure 2I:
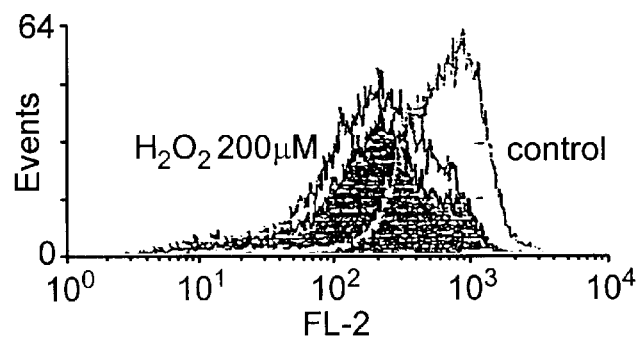
Figure 2J:
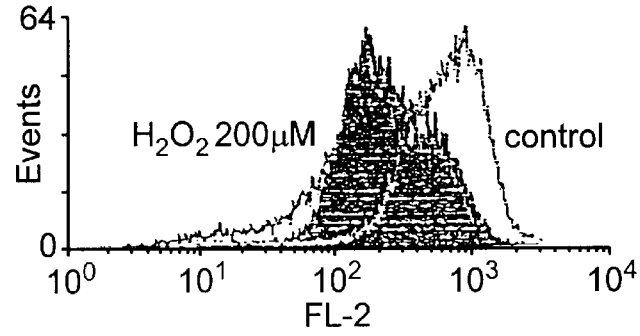

The effects of mitoK$_{ATP}$ channel activation by flow cytometry (FIGS. 2F–J) were further quantified. Incubation with 200 μM $H_2O_2$ for 2 h decreased the red fluorescence and shifted the distribution curve leftward. In agreement with the confocal image analysis, diazoxide prevented the $H_2O_2$-induced dissipation of Δψ in a dose-dependent manner, as shown by the progressive rightward shift of the distribution curve with increasing concentrations of diazoxide (FIGS. 2F–H; F: 20 μM, G: 50 μM, H: 100 μM). 5-HD (500 μM) abolished the effect of diazoxide, and reverted the distribution to that of the $H_2O_2$ group (FIG. 2I). Importantly, 5-HD alone had no effect on Δψ in the absence of diazoxide (FIG. 2J). To confirm the central role of mitoK$_{ATP}$ channels, we examined another mitoK$_{ATP}$ channel opener, pinacidil. Incubation with 100 μM pinacidil was equi-effective to diazoxide in restoring the loss of Δψ induced by 200 μM $H_2O_2$. Moreover, the K$_{ATP}$ blocker, glibenclamide (10 μM, which blocks mitoK$_{ATP}$ channel), reversed the salutary effect of diazoxide.

EXAMPLE 2

Cytoprotective effects of diazoxide in neurons also was evaluated. FIG. 3 shows the results of JC-1 staining in primary cultures of rat cerebellar granule neurons. Staining was conducted as follows: loss of mitochondrial membrane potential (Δψ) was assessed using either a laser scanning confocal microscope or flow cytometry analysis of cells stained with 5,5',6,6'-tetrachloro-1,1',3,3'-tetraethylbenzimidazolecarbocyanide iodine (JC-1, Molecular Probes). Cells were incubated with 2 μg/mL JC-1 for 10 min in 37° C. After washing the dye, cells on dishes were scanned with a confocal microscope at 10× magnification. The dye was excited by the 488 nm line of an argon laser, and the 543 nm line of a helium/neon laser. The red emission of the dye is due to a potential-dependent aggregation in the mitochondria, reflecting Δψ. Green fluorescence reflects the monomeric form of JC-1, occuring in the cytosol after mitochondrial membrane depolarization. The fluorescence intensity of the field was measured using integrated image analysis software (Simple32; Compix, Inc.), which was programmed to automatically detect all areas of red or green fluorescence above background. The data are plotted as mean values of arbitrary units of fluorescence intensity. For flow cytometry analysis, cells were harvested by trypsinization after loading of the dye, and analyzed by FACScan (10,000 cells/sample). The excitation wavelength was 488 nm, and the emission fluorescence for JC-1 was monitored at 530 (FL-1) and 582 nm (FL-2). The flow cytometry data are analyzed using Cell Quest (Becton Dickinson, Immunocytometry Systems). In this protocol, since green fluorescence intensity did not change significantly among groups, we simply plotted the changes in red fluorescence intensity.

Figure 3A:
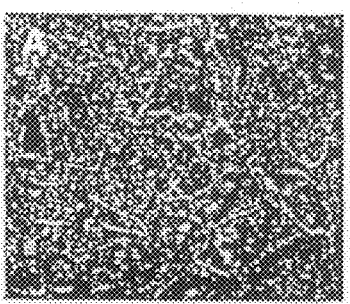
FIG. 3. Mitochondrial membrane potential ($\Delta\psi$) in neonatal rat cerebellar granule neuron. (A) Control cells show predominantly punctate red staining with a fluorescent dye, JC-1, indicative of normal mitochondrial uptake driven by a maintained $\Delta\psi$. (B) Cells exposed to 100 $\mu$M $H_2O_2$ for 1 h lose punctate red staining. (C) 100 $\mu$M diazoxide protects against $H_2O_2$-induced loss of $\Delta\psi$, as shown by the preservation of red signals. (D): The protective effect of diazoxide is blocked by 500 $\mu$M of mitoK$_{ATP}$ channel blocker 5-HD. (E) Quantitative analysis from low power confocal images. Lane 1: $H_2O_2$ 100 $\mu$M, lane 2: $H_2O_2$ 100 $\mu$M+diazoxide 100 $\mu$M, lane 3: $H_2O_2$ 100 $\mu$M+diazoxide 100 $\mu$M+5-HD 500 $\mu$M. Results are expressed as arbitrary units of red fluorescence intensity. The value of control group was 109.98.
Figure 3B:
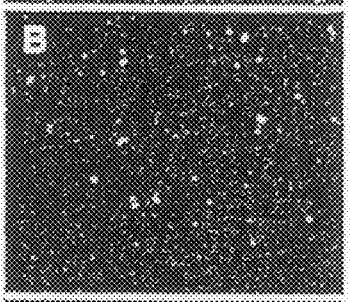
Figure 3C:
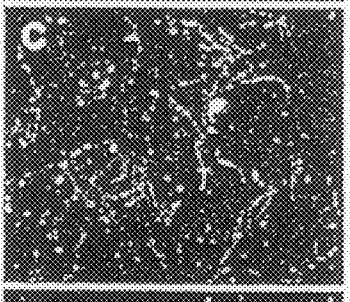
Figure 3D:
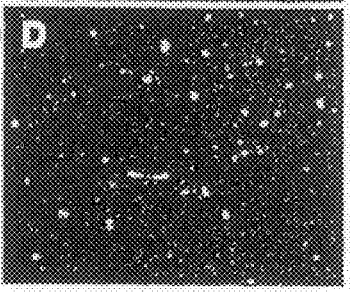
Figure 3E:
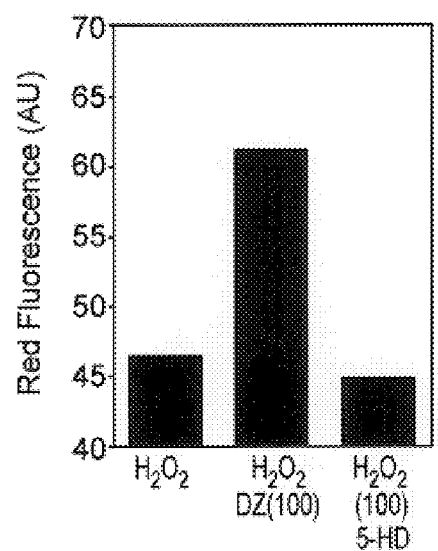

Control cells show punctate red staining (FIG. 3A), indicative of normal mitochondrial uptake driven by Δψ. Cells exposed to 100 μM $H_2O_2$ for 1 h lose punctate red staining (FIG. 3B). Incubation with 100 μM diazoxide protects against $H_2O_2$-induced loss of mitochondrial integrity (FIG. 3C), and the protective effect of diazoxide is blocked by 500 μM 5-HD (FIG. 3D). Quantitative measurements of red fluorescence in neurons (FIG. 3E) confirm the significance of the differences. These findings indicate that cardiac myocytes and neuronal cells share the same anti-apoptotic mechanism in response to mitoK$_{ATP}$ channel agonists.

The findings are noteworthy for several reasons. First, the fact that mitoK$_{ATP}$ channel activation inhibits apoptosis provides further evidence for the central role of these organelles in programmed cell death. The opening of mitoK$_{ATP}$ channels may act quite early in the apoptotic cascade by inhibiting cytochrome c release; such inhibition could result from a decrease in mitochondrial calcium overload, which is reported consequence of diazoxide. Additionally, the potent cytoprotection by mitoK$_{ATP}$ channel recruitment indicates that ischemic preconditioning reflects inhibition of apoptosis in addition to necrosis.

The invention has been described in detail with particular reference to the preferred embodiments thereof. However, it will be appreciated that modifications and improvements within the spirit and teachings of the inventions may be made by those in the art upon considering the present disclosure.

What is claimed is:

1. A method for inhibiting cellular apoptosis, comprising administering to mammalian cells that are undergoing apoptosis, or susceptible to apoptosis, an effective amount of one or more mitoK$_{ATP}$ channel opening compounds.

2. The method of claim 1 wherein the cells are under oxidative stress.

3. The method of claim 1 wherein the cells are cardiac cells.

4. The method of claim 1 wherein the cells are neuronal cells.

5. The method of claim 1 wherein the cells have been identified and selected for treatment to inhibit apoptosis, and the one or more compounds are then administered to the identified and selected cells.

6. The method of claim 1 wherein the one or more compounds increase mitochondrial redox state by at least 30 percent in a standard mitcohondrial redox assay.

7. The method of claim 1 wherein the one or more compounds are diazoxide, pinacidil, nicorandil, and/or BMS 191095.

8. The method of claim 1 wherein administration of the one or more compounds inhibits activation of the mitochondrial apoptotic pathway induced by oxidative stress.

9. The method of claim 1 wherein the cells are human cells.

10. A method for treating a mammal suffering from a disease or disorder that is heart failure, a neurodegenerative disease, spinal cord injury or diabetes, comprising identifying and selecting the mammal on the basis of the disease or disorder, and administering to the mammal an effective amount of one or more mitoK$_{ATP}$ channel opening compounds.

11. The method of claim 10 wherein the mammal is suffering from heart failure.

12. The method of claim 11 wherein the one or more compounds are administered to the mammal within about 6 hours after the mammal has suffered heart failure.

13. The method of claim 1 wherein the one or more compounds are administered to the mammal within about 18 hours after the mammal has suffered heart failure.

14. The method of claim 11 wherein the one or more compounds are administered to the mammal within about 1 week after the mammal has suffered heart failure.

15. The method of claim 1 wherein the mammal is suffering from congestive heart failure.

16. The method of claim 10 wherein the mammal is suffering from a neurodegenerative disease.

17. The method of claim 10 wherein the mammal is suffering from spinal cord injury.

18. The method of claim 10 wherein the mammal is suffering from diabetes.

19. The method of claim 10 wherein the one or more compounds increase mitochondrial redox state by at least 30 percent in a standard mitcohondrial redox assay.

20. The method of claim 10 wherein the one or more compounds are diazoxide, pinacidil, nicorandil, and/or BMS 191095.

21. The method of claim 10 wherein the mammal is a human.

22. A method for treating a mammal suffering from diabetes, comprising administering to the mammal an effective amount of one or more mitoK$_{ATP}$ channel opening compounds.

23. The method of claim 22 wherein the mammal suffering from diabetes is identified and selected for treatment, and then the one or more mitoK$_{ATP}$ channel opening compounds are administered.

24. The method of claim 23 wherein the one or more compounds increase mitochondrial redox state by at least 30 percent in a standard mitochondrial redox assay.

25. The method of claim 23 or 24 wherein the one or more compounds are diazoxide, pinacidil, nicorandil and/or BMS 191095.

26. The method of claim 23 or 24 wherein the mammal is a human.

27. A method for treating a mammal suffering from or susceptible to neuronal cell death or degeneration, comprising identifying and selecting the mammal on the basis of the suffering from or susceptibility to nerve cell death and administering to the selected mammal an effective amount of pinacidil, nicorandil or BMS 191095.

28. The method of claim 27 wherein the mammal is suffering from or has suffered stroke, heart attack, hypoxia, hyploglycemia, brain or spinal cord ischemia, or brain or spinal cord trauma.

29. The method of claim 27 wherein the mammal has suffered from a cardiac arrest neurological deficit.

30. The method of any one of claims 27 through 29 wherein the mammal is a human.

31. A method for treating a mammal suffering from or susceptible to stroke, heart attack, hypoxia, hyploglycemia, brain or spinal cord ischemia, or brain or spinal cord trauma, comprising identifying and selecting the mammal on the basis of the suffering from or susceptibility to stroke, heart attack, hypoxia, hyploglycemia, brain or spinal cord ischemia, or brain or spinal cord trauma, and administering to the selected mammal an effective amount of nicorandil.

32. The method of claim 31 wherein the mammal is suffering from or has suffered from stroke, heart attack, hypoxia, hyploglycemia, brain or spinal cord ischemia, or brain or spinal cord trauma.

33. The method of claim 31 wherein the mammal has suffered from or has suffered a stroke.

34. The method of any one of claims 31 through 33 wherein the mammal is a human.

35. A method for treating a mammal suffering from consequences of stroke, heart attack, or traumatic brain or head injury, comprising administering to a mammal who has suffered stroke, heart attack or traumatic brain or head injury an effective amount of nicorandil.

36. The method of claim 35 wherein the mammal has suffered from a stroke.

37. The method of claim 35 wherein the mammal has suffered from a heart attack.

38. The methods of claim 35 wherein the mammal has suffered from traumatic brain or head injury.

39. The method of any one of claims 35 through 38 wherein the mammal is a human.

* * * * *